May 20, 1969 A. G. J. JULEN Plant Pat. 2,887

BLUEGRASS PLANT

Filed Oct. 12, 1967

United States Patent Office

Plant Pat. 2,887
Patented May 20, 1969

2,887
BLUEGRASS PLANT

Axel Gustaf Jonatan Julen, Karl XI gatan 3,
Svalof, Sweden

Filed Oct. 12, 1967, Ser. No. 675,004
Int. Cl. A01h 5/00
U.S. Cl. Plt.—88 1 Claim

ABSTRACT OF THE DISCLOSURE

A Kentucky bluegrass plant having decumbent and uniform turf characteristics, with a short straw and an angle of repose for the linear leaf blade which approximates ninety degrees. The plant has good resistance to common grass diseases and is a vigorous rhizome producer.

This invention relates to a new and distinct variety of bluegrass plant, the novel characteristics of which reside particularly in the low height of the plant and in its thick and uniform turf.

Several years ago, I discovered the basic plant of the new variety on cultivated land in the vicinity of Svalof in southern Sweden. Plant material from the variety was taken to the nursery and was asexually reproduced by me with the planting of rhizomes. Seeds from the thus reproduced variety were sown in field plots for evalution and testing. Subsequent testing programs have been conducted on a comprehensive scale both in Sweden and in the temperate zone of North America.

The instant bluegrass has several distinctive characteristics which are not evident in other bluegrasses. Of special moment are its dwarf charcateristics, the thickness and uniformity of the turf, and an aggressive rhizome system. The bluegrass exhibits good resistance to low mowing, disease, and cold weather, and these factors coupled with its small size render the plant eminently suitable as a lawn grass. In addition, the plant has demonstrated good pasture grass characteristics, including even production throughout the summer and fall, persistency, and resistance to trampling and grassing.

A primary object of the invention is to provide a new and distinct bluegrass plant having the desirable characteristics referred to above and to be described in detail below.

Figure 1:
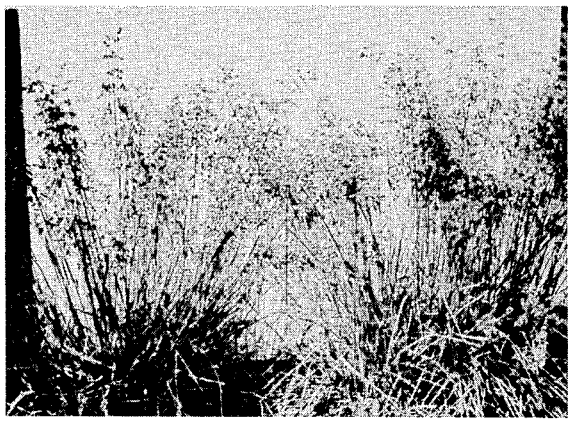
Figure 2:
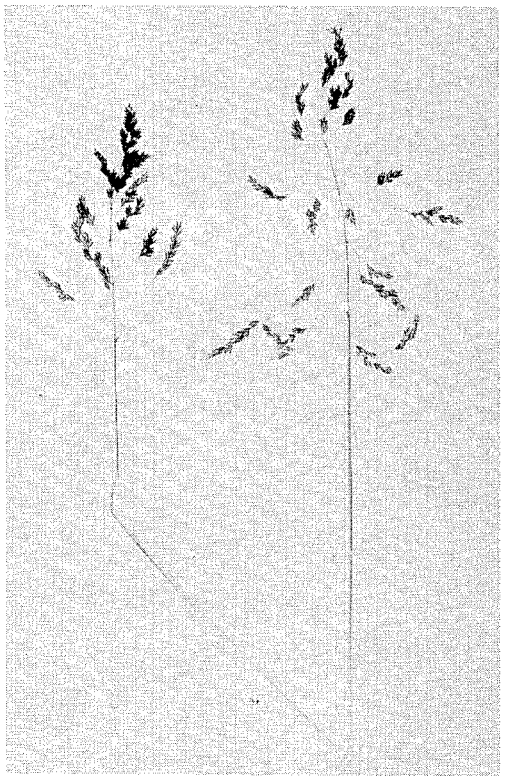

Other objects and advantages of the invention will become apparent from the following detailed description when taken in conjunction with the accompanying illustrations, in which:

FIGURE 1 shows two plants of the new variety immediately prior to the flowering stage; and FIGURE 2 shows typical panicles of the variety, with a young panicle just before the flowering stage on the left and an old panicle at the time of speed ripening on the right.

The new variety is a perennial Kentucky bluegrass (*Poa pratensis*, f. *vulagris*, Gaud.), but with a shorter straw than most types belonging to this species. Even after full development, the straw rarely reaches over 60 cm. in length. The bottom internodes are extremely short, and the lower leaves therefore develop closer to the ground than the leaves of other plants in the species.

The instant bluegrass is asexually reproduced by rhizomes. The plant is highly apomictic, and therefore, genetically stable. The offspring are extremely uniform, and almost every plant is an exact copy of the mother plant. Following the establishment of the plant, an extremely aggressive rhizome system is produced. As an illustration, during a root production study at Washington State University in 1965, tests were conducted in both June and September with respect to root plugs of the instant bluegrass as compared with similar plugs of Merion, Newport and Delta bluegrasses. Each of the grasses was mowed at heights of one inch and one-half inch, and the root plugs were exhumed, washed and weighed. The results are shown in Table 1.

TABLE 1.—ROOT PRODUCTION COMPARISONS

| Variety | One Inch Cut (oz.) | | One Half Inch Cut (oz.) | |
|---|---|---|---|---|
| | June wgt. | Sept. wgt. | June wgt. | Sept. wgt. |
| The instant | 17.2 | 19.2 | 14.9 | 14.1 |
| Merion | 12.2 | 20.3 | 10.3 | 14.4 |
| Newport | 10.7 | 17.4 | 9.6 | 16.9 |
| Delta | 11.0 | 12.9 | 7.1 | 10.5 |

The aggressive characteristics of the instant bluegrass are evident particularly from a comparison of the June weights of the root plugs.

*Morphological description*

Morphological characteristics of the instant bluegrass are as follows:

Roots: Subsoil rhizomes with short internodes. The plant exhibits a rich root system as well as a dense sward of shoots.

Leaves: Ascending tufts; up to 30 cm. in length and 4 to 6 mm. in width; straw leaves 5 to 7 cm. in length and 3 to 6 mm. in width. Young leaves are folded, later on flattening up. The ligule is very short.

Straw: Round and short. Even after full development the straw rarely is over 60 cm. in length.

Panicle: Triangularly shaped, having a base of about 8 to 12 cm. and a height of about 10 to 14 cm. The panicle exhibits 5 to 6 internodes with 4 or 5 branches at each node and up to 6 clusters of spikelets on each branch. Each spikelet consists of 5 to 6 flowers. The edges of the glumes are very thin and colorless. Inside the edge area is a violet strip, while the major portion of the glume is clear green. Upon flowering, the violet strip turns green, and the entire panicle gives a greyish-green impression.

Seed: The instant bluegrass is large seeded, containing approximately 1,130,000 seeds per pound. For comparison purposes, Merion bluegrass contains about 2,100,000 seeds per pound, and Common bluegrass contains about 1,600,000 seeds per pound.

*Growth habit*

The instant bluegrass exhibits individuality in both vertical and lateral growth characteristics. Vertical growth takes place through the elongation of the sheating base of the leaf and slight vertical elongation of the linear blade. The distance of petiole elongation between the basal internode and the lowest leaf collar is less than 1 cm. The plant exhibits a decumbent characteristic different from most other bluegrass types.

Another distinctive characteristic is the angle of repose of the linear leaf blade. In most bluegrass types this angle is somewhat in excess of ninety degrees. The leaf of the new variety, however, maintains an almost constant ninety degree angle of repose. The dwarf characteristic and the ninety degree angle of repose for the linear leaf blade combine to render the plant particularly useful as a lawn grass. The lawn may be mowed quite short while still leaving a sufficient number of leaves for further development and sufficient leaf area for normal assimilation.

*Cytological Characteristics*

The chromosome number of the instant bluegrass ranges between about 72 and about 76. The chromosome number deviates even in different aprts oft he same plant, however, and numbers as high as 122 have been observed. This variation in chromosome number does not affect the morphology of the plant.

*Turf density*

Comparative density data is listed in Table 2. The density ratings were taken in both 1964 and 1965 at various locations in the temperate zone of North America.

TABLE 2.—TURF DENSITY COMPARISONS FOR THE INSTANT AND OTHER BLUEGRASSES—1964-1965

[Scale: 1=highest density; 6=lowest density]

| | N.J. | | Minn. | | Conn. | | Wash. | | Ill. | | N.Y. | |
|---|---|---|---|---|---|---|---|---|---|---|---|---|
| Variety | '64 | '65 | '64 | '65 | '64 | '65 | '64 | '65 | '64 | '65 | '64 | '65 |
| The instant | 1 | 1 | 1 | 1 | 2 | 2 | 1 | 1 | 1 | 1 | 1 | 1 |
| Merion | 2 | 3 | 1 | 1 | 1 | 1 | 2 | 2 | 1 | 1 | 1 | 1 |
| Windsor | 3 | 5 | 2 | | | 3 | 3 | 3 | | 3 | | |
| Newport | 4 | 4 | | | 3 | 5 | 3 | 3 | | | | |
| Common | 5 | | 3 | | 3 | 6 | 4 | 4 | | | | |
| Park | | | | 3 | 3 | 4 | | | | 2 | | |

The data shows that the instant bluegrass maintained a high turf density throughout 1964 and 1965. The density was equal to the density of Merion bluegrass in Minnesota, Illinois and New York, and exceeded that of Merion in New Jersey and Washington. In the Connecticut tests, the density of Merion was slightly above that of the instant.

*Turf color*

The leaf color of the instant bluegrass approximates the dark blue-green color of Merion bluegrass. However, the instant bluegrass retains its color considerably later in the fall than Merion or any other known bluegrass variety. The results of color comparisons between the instant and other bluegrass varieties are given in Table 3.

TABLE 3.—TURF COLOR COMPARISONS FOR THE INSTANT AND OTHER BLUEGRASSES—1964-1965

[Scale: 1=darkest green; 6=lightest green]

| | N.Y. | | Conn. | | Ohio | | Minn. | | Wash. | |
|---|---|---|---|---|---|---|---|---|---|---|
| | 1964 | 1965 | 1964 | 1965 | 1964 | 1965 | 1964 | 1965 | 1964 | 1965 |
| The instant | 1 | 1 | 1 | 2 | 1 | 1 | 1 | 1 | 3 | 2 |
| Merion | 1 | 1 | 2 | 3 | 3 | 2 | | 2 | 1 | 1 |
| Windsor | | | 4 | 4 | 2 | | 3 | | | |
| Newport | | | | 6 | 4 | 3 | | | 2 | 3 |
| Park | | | | 5 | 4 | 4 | | 3 | | |
| Common | | | 3 | 1 | 6 | 5 | 2 | 4 | 4 | |

In the spring, the instant blue grass acquires its color slightly later than Common and about 1 day after Merion.

*Leaf Texture*

The instant bluegrass has a medium leaf texture which is slightly finer than Merion bluegrass, as shown in Table 4.

TABLE 4.—LEAF TEXTURE COMPARISONS FOR THE INSTANT AND OTHER BLUEGRASS VARIETIES—1964-1965

[Scale: 1=coarse texture; 5=medium texture; 10=very fine texture]

| | Ohio | | Conn. | | Minn. | | Calif. | | Wash. | |
|---|---|---|---|---|---|---|---|---|---|---|
| | 1964 | 1965 | 1964 | 1965 | 1964 | 1965 | 1964 | 1965 | 1964 | 1965 |
| The instant | 5.0 | 5.7 | 5 | | | 6.0 | | 7.0 | 7.0 | 6.0 |
| Merion | 5.5 | 5.0 | 5 | | | 5.5 | | 5.5 | 5.0 | 5.0 |
| Windsor | 5 | | 5 | | | | | | 6.0 | 6.2 |
| Park | 5.3 | 6.0 | 5 | | | | | | 6.0 | 6.0 |
| Newport | 5.0 | 5.0 | 5 | | | 5.0 | | | 5 | 5.2 |
| Common | 5.2 | 5.7 | 5 | | | | | | 6.0 | 6.0 |

*Disease resistance*

The new variety exhibits moderate to good resistance to stripe smut, rust and mildew, and very good resistance to leafspot and *Fusarium roseum*. A comparison of the instant and other bluegrasses for resistance to rust, leafspot and mildew is given in Tables 5, 6 and 7.

TABLE 5.—RELATIVE COMPARISON OF RUST RESISTANCE LEVEL FOR THE INSTANT AND OTHER BLUEGRASS VARIETIES—1964-1965

[Scale: 1=most resistant; 4=least resistant]

| | Ind. | | Wash. | | Minn. | | Ill. | |
|---|---|---|---|---|---|---|---|---|
| | 1964 | 1965 | 1964 | 1965 | 1964 | 1965 | 1964 | 1965 |
| The instant | | 2 | 1 | 2 | 2 | | 1 | |
| Merion | | | 3 | 4 | 3 | | 2 | |
| Newport | | 1 | 2 | 3 | | | | |
| Windsor | | 2 | | | | | | |
| Cougor | | | | 1 | | | | |
| Common | | | 3 | | 1 | | | |
| Prato | | 4 | | | | | | |
| Delta | | 3 | | 4 | | | | |

TABLE 6.—RELATIVE COMPARISON OF LEAFSPOT RESISTANCE LEVEL FOR THE INSTANT AND OTHER BLUEGRASS VARIETIES—1964-1965

[Scale: 1=most resistant; 5=least resistant]

| | N.J. | | Ohio | | Minn. | | N.Y. | | Wash. | |
|---|---|---|---|---|---|---|---|---|---|---|
| | 1964 | 1965 | 1964 | 1965 | 1964 | 1965 | 1964 | 1965 | 1964 | 1965 |
| The instant | 2 | 1 | 1 | 2 | | 2 | 1 | 1 | 4 | 3 |
| Merion | 1 | 2 | 2 | 1 | | 1 | 1 | 1 | 1 | 1 |
| Newport | 4 | 3 | 4 | 3 | | | | 2 | 2 | 2 |
| Park | | | | 4 | | | | | | |
| Windsor | 3 | | 3 | | | | | | | |
| Common | 5 | 4 | 5 | 5 | | | | | 3 | 4 |

TABLE 7.—RELATIVE COMPARISON OF POWDERY MILDEW RESISTANCE LEVEL FOR THE INSTANT AND OTHER BLUEGRASS VARIETIES-1965.

[Scale: 1=most resistant; 3=least resistant]

| | Indiana, 1965 | California, 1965 |
|---|---|---|
| The instant | 1 | 3 |
| Merion | 2 | 1 |
| Newport | | 2 |
| Windsor | 1 | |

The instant bluegrass has demonstrated extremely good winter hardiness characteristics. The dense and leafy sward of the plant, the dwarf characteristics and resistance to low mowing, its color retention properties, disease resistance and winter hardiness combine to produce an extremely valuable lawn grass. The plant also has demonstrated good resistance to trampling, and high and even leaf production throughout the summer and fall. These latter characteristics render the new variety extremely suitable as a pasture grass.

What is claimed is:

1. A new and distinct variety of bluegrass plant substantially as described and illustrated, characterized particularly by small size, thick and uniform turf, and vigorous production of rhizomes.

No references cited.

ROBERT E. BAGWILL, *Primary Examiner.*

UNITED STATES PATENT OFFICE

CERTIFICATE OF CORRECTION

Plant Patent No. 2,887 May 20, 1969

Axel Gustaf Jonatan Julen

It is certified that error appears in the above identified patent and that said Letters Patent are hereby corrected as shown below:

Column 1, line 55, "speed" should read -- seed --. Column 3, line 12, "aprts oft he" should read -- parts of the --. line 59, "1 day" should read -- 10 days --.

Signed and sealed this 9th day of September 1969.

(SEAL)
Attest:

Edward M. Fletcher, Jr.
Attesting Officer

WILLIAM E. SCHUYLER, JR.
Commissioner of Patents